United States Patent
Sonara et al.

(10) Patent No.: US 12,260,312 B2
(45) Date of Patent: Mar. 25, 2025

(54) SOFT-SENSOR TO MEASURE PH OF TREATED SEAWATER

(71) Applicant: Saudi Arabian Oil Company, Dhahran (SA)

(72) Inventors: Prafulchandra Bhavanbhai Sonara, Abqaiq (SA); Abdulrahman S. Al Johar, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 1118 days.

(21) Appl. No.: 17/140,224

(22) Filed: Jan. 4, 2021

(65) Prior Publication Data

US 2022/0215230 A1 Jul. 7, 2022

(51) Int. Cl.
*G06N 3/042* (2023.01)
*B01D 19/00* (2006.01)
(Continued)

(52) U.S. Cl.
CPC ......... *G06N 3/042* (2023.01); *B01D 19/0005* (2013.01); *B01D 19/0063* (2013.01); *C02F 1/008* (2013.01); *C02F 9/00* (2013.01); *C09K 8/845* (2013.01); *E21B 41/00* (2013.01); *G06N 3/10* (2013.01); *C02F 1/001* (2013.01); *C02F 1/20* (2013.01); *C02F 1/66* (2013.01); *C02F 2101/10* (2013.01); *C02F 2103/08* (2013.01); *C02F 2209/001* (2013.01);
(Continued)

(58) Field of Classification Search
None
See application file for complete search history.

(56) References Cited

U.S. PATENT DOCUMENTS 8,449,656 B2 * 5/2013 Wu ............................ C02F 1/20
96/201
8,678,080 B2 * 3/2014 Curole .................... E21B 43/20
166/305.1
(Continued)

FOREIGN PATENT DOCUMENTS

CN S5916584 1/1984
CN 105067542 6/2018
(Continued)

OTHER PUBLICATIONS

Aguirre et al., "Development of soft sensors for permanent downhole Gauges in deepwater oil wells" Jun. 22, 2017, doi: 10.1016/j.conengprac.2017.06.002, pp. 83-99. (Year: 2017).*
(Continued)

*Primary Examiner* — Philip J Chea
*Assistant Examiner* — Bin Qing Zheng
(74) *Attorney, Agent, or Firm* — Fish & Richardson P.C.

(57) ABSTRACT

Systems and methods include a computer-implemented method for predicting pH of seawater. A model is generated that is configured to predict a power of hydrogen (pH) of treated seawater. Generating the model includes correlating process parameter values and historical data of seawater processing plants of oil and gas reservoirs. Upstream parameters of the seawater plant are received by a soft sensor pH predictor installed at a seawater plant. A pH of seawater being processed by the seawater plant is predicted using the model and neural network software of the soft sensor pH predictor.

20 Claims, 5 Drawing Sheets

(51) Int. Cl.
| | |
|---|---|
| *C02F 1/00* | (2023.01) |
| *C02F 1/20* | (2023.01) |
| *C02F 1/66* | (2023.01) |
| *C02F 9/00* | (2023.01) |
| *C02F 101/10* | (2006.01) |
| *C02F 103/08* | (2006.01) |
| *C09K 8/84* | (2006.01) |
| *E21B 41/00* | (2006.01) |
| *G06N 3/10* | (2006.01) |

(52) U.S. Cl.
CPC .... *C02F 2209/006* (2013.01); *C02F 2209/02* (2013.01); *C02F 2209/06* (2013.01); *C02F 2209/38* (2013.01); *C02F 2209/40* (2013.01); *C02F 2209/42* (2013.01)

(56) References Cited

U.S. PATENT DOCUMENTS

| | | | | |
|---|---|---|---|---|
| 9,341,058 | B2* | 5/2016 | Keizer | C02F 1/008 |
| 9,579,700 | B2 | 2/2017 | Osborne | |
| 10,960,964 | B2* | 3/2021 | Richardson | C02F 1/76 |
| 2012/0067791 | A1 | 3/2012 | Yokokawa et al. | |
| 2016/0368800 | A1* | 12/2016 | Eriksen | E21B 43/01 |
| 2018/0208480 | A1* | 7/2018 | Chambhare | C02F 1/444 |
| 2020/0320448 | A1* | 10/2020 | Machida | G06Q 10/067 |

FOREIGN PATENT DOCUMENTS

| | | | | |
|---|---|---|---|---|
| CN | 111718029 A | * | 9/2020 | E21B 43/01 |
| EP | 2508249 | | 10/2012 | |
| JP | 2009204272 | | 9/2009 | |
| JP | 2010099658 | | 5/2010 | |
| WO | WO 2013115108 | | 8/2013 | |
| WO | WO 2014129727 | | 8/2014 | |

OTHER PUBLICATIONS

Li et al., "Retrieving monthly and interannual total-scale pH (pHT) on the East China Sea shelf using an artificial neural network: ANN-pHT-v1" Oct. 27, 2020, doi: 10.5194/gmd-13-5103-2020, pp. 5103-5117. (Year: 2020).*

De Maria et al., "Oxygen removal from injection seawater in offshore platforms: vacuum tower versus membrane deaeration technology" Jun. 21-24, 2017, https://cannonartes.com/wp-content/uploads/2022/07/2017-Impiantistica-Italiana-MDA-vs-VT.pdf. (Year: 2017).*

Nasr et al., "Performance Evaluation of El-Agamy Wastewater Treatment Plant-Egypt" Dec. 15-17, 2014, doi: 10.13140/RG.2.1.1533.8089. (Year: 2014).*

Dunbar et al., "Improving Refinery Performance: Process and Control Information from Step Testing", https://www.emerson.com/documents/automation/white-paper-improving-refinery-peformance-process-control-information-from-step-testing-pss-en-67718.pdf. (Year: 2004).*

Sprenkel, "A Discussion on Chemicals used in Seawater Treatment & Re-injection Systems", Jun. 3, 2020, https://www.linkedin.com/pulse/discussion-chemicals-used-seawater-treatment-systems-marcus-sprenkel. (Year: 2020).*

Durdevic, "Potential for Real-Time Monitoring and Control of Dissolved Oxygen in the Injection Water Treatment Process", Jun. 2018, IFAC-PapersOnLine, vol. 51, Issue 8, pp. 170-177, doi: 10.1016/j.ifacol.2018.06.373, (Year: 2018).*

PCT International Search Report and Written Opinion in International Appln. No. PCT/US2022/011165, dated Apr. 29, 2022, 12 pages.

* cited by examiner

SOFT-SENSOR TO MEASURE PH OF TREATED SEAWATER

BACKGROUND

Technical Field

The present disclosure applies to techniques for measuring pH, or the power of hydrogen, which is a measure of the concentration of hydrogen ions (or the acidity) in a solution.

Background

Conventional techniques that measure pH, such as in seawater associated with oil wells injection, are typically based on a physical sensor that is installed in the field. The sensor can be connected to either a control system or a local display to show a measured value of pH. Physical sensors installed in field can be costly and such sensors typically require the modification of an existing arrangement to allow sampling. These sensors typically need regular maintenance and calibration in order to maintain satisfactory operation. Conventional approaches for measuring pH typically use a physical pH analyzer. Physical analyzers are costly, they need extensive maintenance and their accuracy needs to be checked by regular calibration. If the analyzer is not calibrated regularly, it will start giving incorrect readings without any alarm. If controls are based on the analyzer measurements then the whole control will start behaving abnormally which can lead to severe consequences.

Controlling the pH of treated seawater is an important aspect of processing plants. To control the pH of treated seawater, for example, the pH first needs to be measured. Controlling the pH can also facilitate the control of sulfur trioxide, a chemical compound of sulfur and oxygen. Concentrations of $SO_3$ sulfite, for example, can affect bacterial growth and corrosion. Higher pH values that exceed a recommended value can lead to scale formation in pipelines. Lower pH values below a recommended value can lead to greater $SO_2$ particulates, which in turn can cause higher bacterial growth and pipeline corrosion.

SUMMARY

The present disclosure describes techniques for using soft-sensors to measure the power of hydrogen (pH) in seawater, such as at a processing plant. In some implementations, a computer-implemented method includes the following. A model is generated that is configured to predict a power of hydrogen (pH) of treated seawater. Generating the model includes correlating process parameter values and historical data of seawater processing plants of oil and gas reservoirs. Upstream parameters of the seawater plant are received by a soft sensor pH predictor installed at a seawater plant. A pH of seawater being processed by the seawater plant is predicted using the model and neural network software of the soft sensor pH predictor.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method/ the instructions stored on the non-transitory, computer-readable medium.

The subject matter described in this specification can be implemented in particular implementations, so as to realize one or more of the following advantages. Soft-sensors can be used to measure the pH of water at any processing plant that requires the measurement of pH in water. The use of soft-sensors can save capital costs as the soft-sensors do not require additional hardware. If a single pH analyzer costs around US $10,000, for example, the pH analyzer capital costs for a Processing Plant Q with 28 treatment modules would be US $280,000. This cost would be avoided using soft-sensors instead. Soft-sensors do not need regular maintenance and calibration and this can also result in a recurring savings of US $50,000 every year. The use of soft-sensors can also optimize dosing of $SO_2$ solutions, which will result in saving US $250,000 per year at Processing Plant Q in the area of maintenance, transportation and infrastructure (T&I) costs of $SO_2$ plants, and reduced boiler rental.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

Like reference numbers and designations in the various drawings indicate like elements.

DETAILED DESCRIPTION

The following detailed description describes techniques for using soft-sensors to measure power of hydrogen (pH) in seawater. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

In some implementations, Big Data analytics can be used with Neural Network technology to develop soft sensors to predict pH value of treated seawater. The predictions can be made based on the process parameter values and historical data. Physical sensors are not required, which can save the costs of physical installations and regular calibration.

Figure 1:
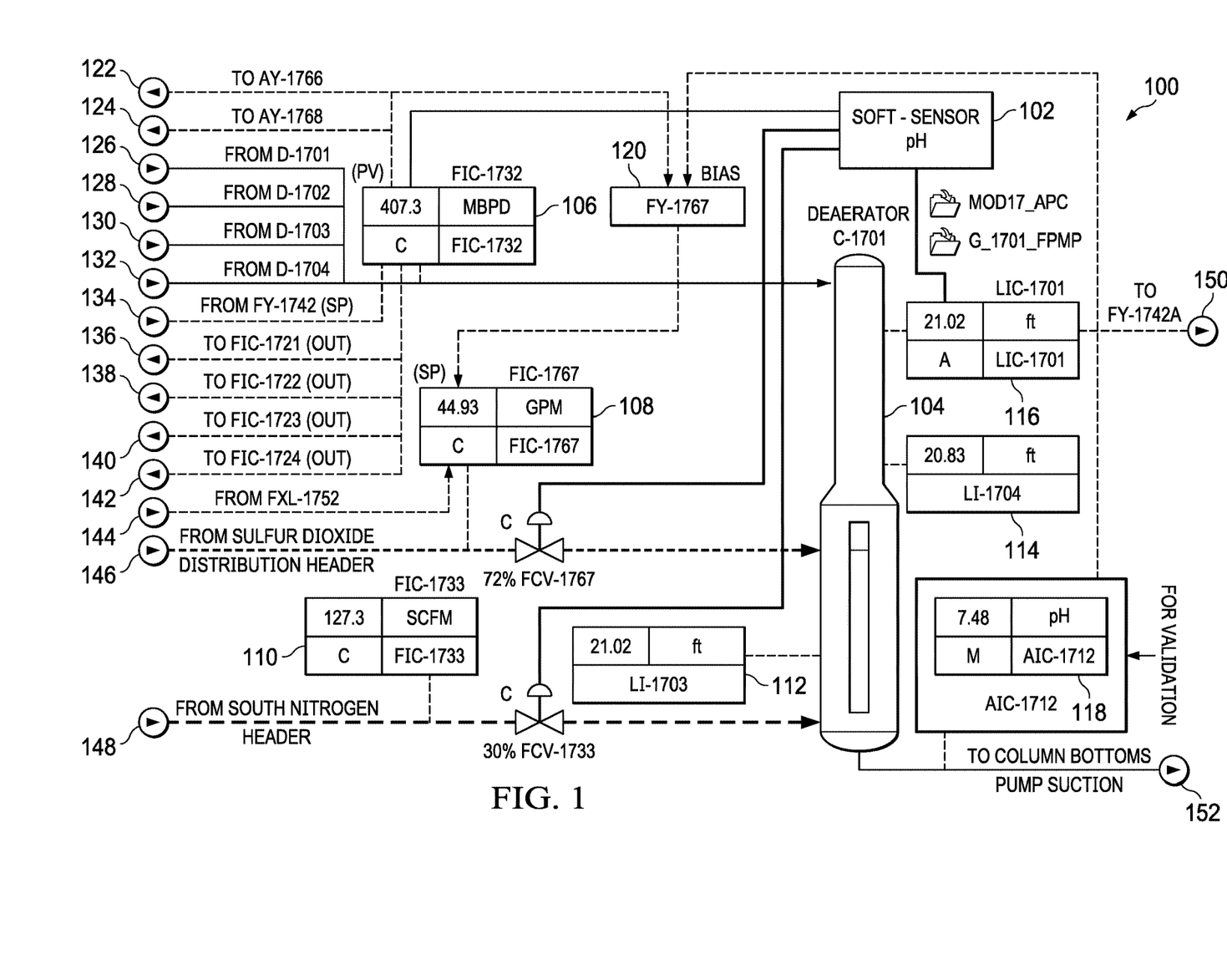
FIG. 1 is schematic diagram showing an example of a power of hydrogen (pH) soft-sensor that is incorporated into a Sea Water Plant (SWP), according to some implementations of the present disclosure.

FIG. 1 is schematic diagram showing an example of a pH soft-sensor 102 that is incorporated into a Sea Water Plant (SWP) 100, according to some implementations of the present disclosure. The SWP 100 can treat seawater, for example. At the SWP 100—Treatment Modules the dissolved oxygen (DO) removal processes can include the injection of $N_2$ gas and a $SO_2$ solution. These processes also affect the pH of seawater. Based on experience using and operating the treatment modules, it can be determined that the pH of seawater at the outlet of a deaerator 104 depends on many process conditions of the deaerator 104 and its upstream parameters. The upstream parameters can include, for example, the total seawater flow into the deaerator, the seawater flow through each filter, the temperature of the seawater, the flow of $N_2$ gas that is injected, the flow of $SO_2$ solution that is injected, and the level of seawater in deaerator.

After treatment at the SWP 100, seawater can be injected into an oil and gas reservoir to maintain its pressure. Prior to injection, an important seawater treatment is to remove DO from seawater and maintain pH between 6.9 and 7.2. Normal seawater pH values range between 7.5 and 8.4, and the recommended range of treated seawater is between 6.9 and 7.2 (for example, to maintain the pH around a neutral pH value of 7.0). The $SO_2$ solution can serve as an oxygen scavenger and reduce pH of the seawater. However if the $SO_2$ solution is over-injected, higher $SO_3$ particulates in treated seawater can lead to higher Sulfur Reducing Bacteria (SRB), which in turn will cause higher corrosion.

Neural network software, such as Delta V Neural software, can be installed in the SWP control system. The neural network software can monitor the upstream parameters previously mentioned. Once process stability is achieved, a step test can be conducted. Under the step test, a single parameter at a time can be changed in steps of 10% within allowable ranges. The impact of the change can be monitored on all the upstream parameters at the same time that the pH is measured. Step test processes can be repeated for all the upstream parameters, and the data results can be collected. The step test can be monitored manually so that any inconsistent data points or outlier can be identified and rejected. As required, the step-test can be repeated as needed. After completion of step test, the data results can be analyzed, and a model can be created. The model can be configured and used to accurately predict the pH of treated seawater. Predicted pH values can occasionally be reconfirmed with actual lab sampling or through a physical pH analyzer. Elements of the SWP 100 include a PID flow controller 106, a PID flow controller 108, a PID flow controller 110, a level indicator 112, a level indicator 114, a PID level controller 116, a pH analyzer 118, mathematical block 120, a signal to other block 122, a signal to other block 124, a deaerator feed 126, a deaerator feed 128, a deaerator feed 130, a deaerator feed 132, a controller setpoint 134, a controller out 136, a controller out 138, a controller out 140, a controller out 142, a controller in 144, an $SO_2$ solution inlet 146, an $N_2$ gas inlet 148, a controller out 150, and a treated water outlet.

Figure 2:
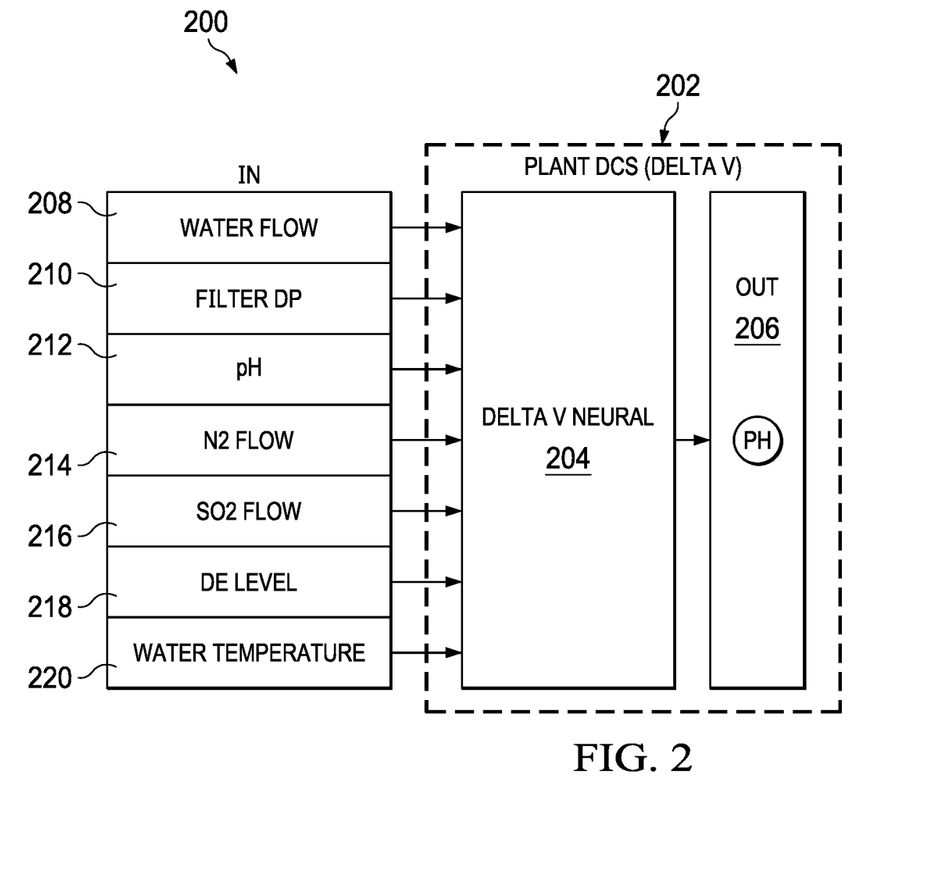
FIG. 2 is a block diagram showing an example of a pH soft-sensor system, according to some implementations of the present disclosure.

FIG. 2 is a block diagram showing an example of a pH soft-sensor system 200, according to some implementations of the present disclosure. The system 200 includes a plant Distributed Control System (DC S) 202, for example, using Delta V neural software 204 to predict pH 206. For example, a primary function of the system 200 is the development and use of a soft sensor to predict pH of treated seawater, which is specifically relevant for water processing plants. Implementations of the system 200 can make use of existing infrastructures available in processing plants. For example, typical modern processing plants involve in seawater treatment are expected to have a DCS and field sensors to measure and control process parameters such as pressure, temperature, flow, and level.

The upstream parameters can include, for example, a total water (for example, seawater) flow 208 into the deaerator, filter differential pressures (DP) 210, the pH 212, an $N_2$ gas flow 214 that is injected, an $SO_2$ solution flow 216 that is injected, a deaerator (DE) level 218 of seawater in the deaerator, and a water temperature 220 (for example, temperature of the seawater). The seawater flow through each filter can also be used.

As an example, the SWP 100 can be a seawater processing plant that includes an infrastructure including a DCS and field sensors. At a specific SWP 100, under a pilot project, Delta V neural software was used to develop and predict the pH of treated seawater based on past data. Delta V neural software, for example, can include commercially available software which can take up to 20 process inputs and generate output based on past data. At the specific SWP 100, for example, Delta V Neural software was used. However, in practice, any commercially available neural software can be used to develop a model for pH based on past data.

PH Soft-Sensor Model and Assumptions

Seawater used in the deaerator can basically be raw seawater. The seawater's pH can be assumed to be same as that of seawater available from a sea (for example, the Arabian Sea). Enough empirical evidence is available to show that the pH of naturally available freshwater or seawater remains constant over a long period of time. Generally, the pH of the Arabia Sea's seawater is always around 7.8 at 25 degrees Celsius. Enough empirical evidences also exists that shows that the pH of seawater is highly dependent on its temperature. These empirical evidentiary assumptions can be used to develop a neural model that can predict pH of treated seawater.

As previously mentioned, treatment of the seawater at the SWP 100 is required to maintain the pH of treated seawater between 6.9 and 7.2. To control the pH within this range, an $SO_2$ solution with a 0.5% concentration (also called sulfurous acid $H_2SO_3$) in seawater can be injected. The $SO_2$ solution is highly acidic with a very low pH value. When the solution is mixed with seawater in the bottom of the deaerator, for example, the pH of the seawater can be reduced from 7.8 to a lower value (for example, in a required range of 7.1). Based on empirical evidence as previously described (and a common sense assumption that higher seawater flow requires more $SO_2$ solution to reduce the pH of treated seawater in a recommended range), a model was developed that can predict the correct value of pH.

Field sensors as previously described were verified as available and working satisfactorily. All the field sensors were connected to plant DCS. A temporary PH analyzer was used initially for developing the model. Once the model was ready, temporary PH analyzer was removed. If cases in which a temporary pH analyzer is not available, laboratory analysis can be done to measure and manually enter pH. Neural network software can also be installed in the DCS.

Once a plant is operating normally and the process is stable, a step test can be conducted. Input parameters, including controllable parameters, can include water flow, $N_2$ flow, and $SO_2$ flow, among others.

During step test, one controllable parameter can be selected. Values of the one parameter can be changed in steps, for example, of approximately 1 to 2% to a maximum upper limit. Then, the values can be changed in steps, for example, of 1 to 2% down to a lower limit. All other parameters can be maintained at their normal operating values. As an example, at the SWP 100, normal operating value of water flow is 400 thousands of barrels per day (MBD), with lower limit of 320 MBD and an upper limit of 480 MBD. During step test, flow is changed from 400 MBD to 405 MBD then 410 MBD, and so on, until an upper limit of 480 MBD is reached. After reaching the upper limit, flow can be reduced in steps, such as to 475 MBD and then 470 MBD, until lower a lower limit of 320 MBD is reached. After each step change, the process can be allowed to become stabilized before the next step is initiated.

Delta V neural software can record all of the parameters including pH values. If a temporary pH analyzer is not available, then laboratory samples can be collected at the end of each step, and their values can be entered manually.

After completion of the step test of first parameter, the same test can be repeated for the remaining parameters while keeping other parameters at normal operating values. After completion of the step test, all recorded values can be analyzed. Delta V neural software can provide recommended values of weights of the nodes. Once the recommended weights are fed in, the model can be ready to predict PH. The values can be validated using laboratory analysis or physical analyzer values.

The steps can be generalized for any water processing plant with appropriate changes. To generalize the process and apply the concept at any plant, proper understanding of process at specific plants is required. Measurements of all relevant parameters that have impact on pH of seawater are assumed to be available at the plant DCS. Step tests need to be conducted when the plant is operating in stable condition.

In some implementations, technical specifications of pH soft-sensor for treated sea water include the following. The soft-sensor is a software algorithm model that predicts the value of pH in treated seawater based on process parameter values. The make the prediction, the algorithm model uses historical data of process parameters and pH values. The predictable range of pH values can be, for example, a pH of 4-11. The seawater can have a temperature in the range of 10 degrees to 45 degrees Celsius. The chlorine can be 2 parts per million (PPM). A step test can be conducted to collect data and create algorithm-based model to predict the pH of the treated seawater. Predicted values of pH can be validated by using either an actual pH analyzer or by laboratory analysis.

Figure 3:
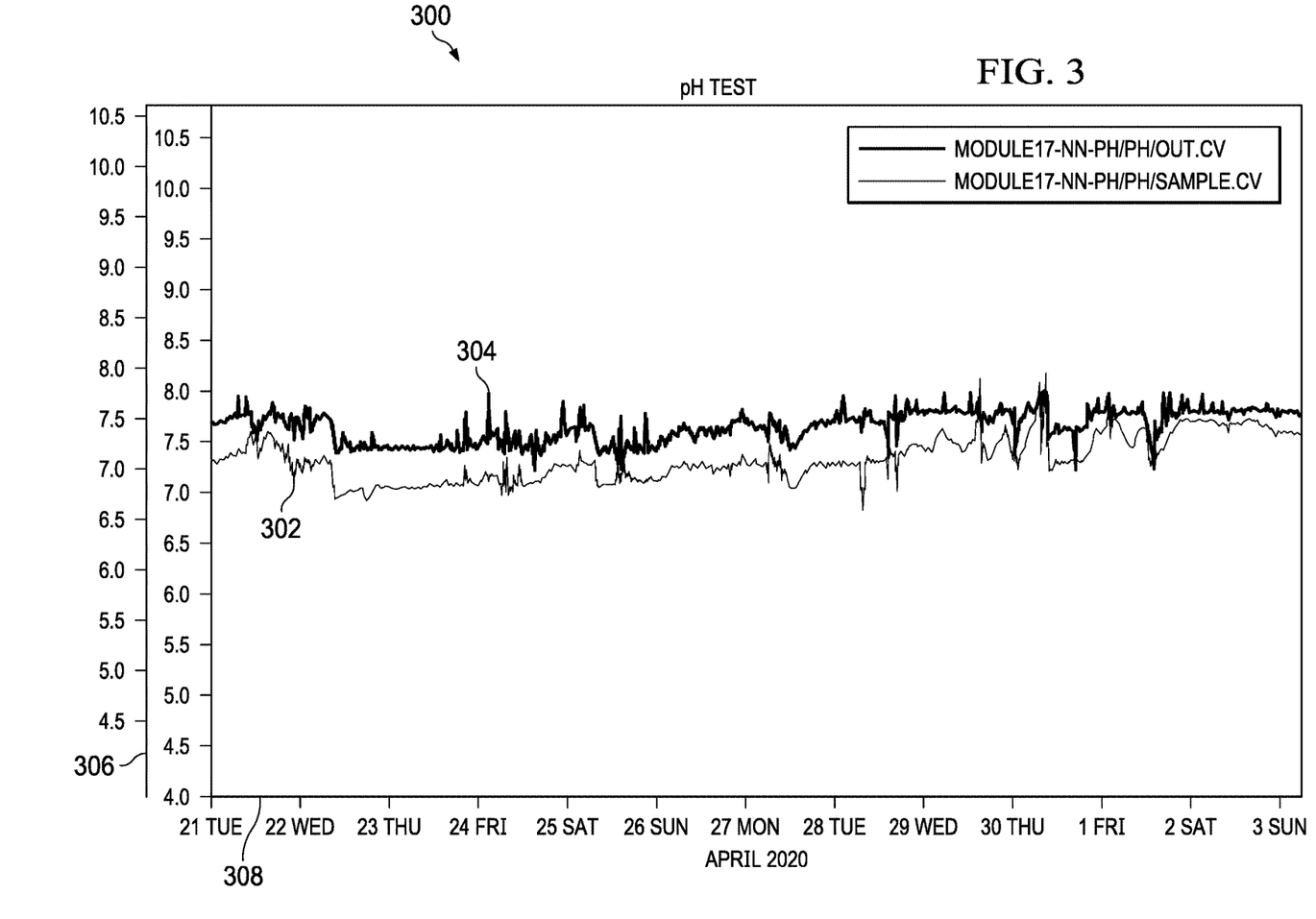
FIG. 3 is a graph showing examples of predicted and actual values of pH, according to some implementations of the present disclosure.

FIG. 3 is a graph 300 showing examples of predicted and actual values of pH, according to some implementations of the present disclosure. For example, plot 302 shows actual pH values 306 of a sample over time 308. For example, plot 304 shows predicted pH values 304 over time 308, for example, corresponding to a predicted pH 206.

Figure 4:
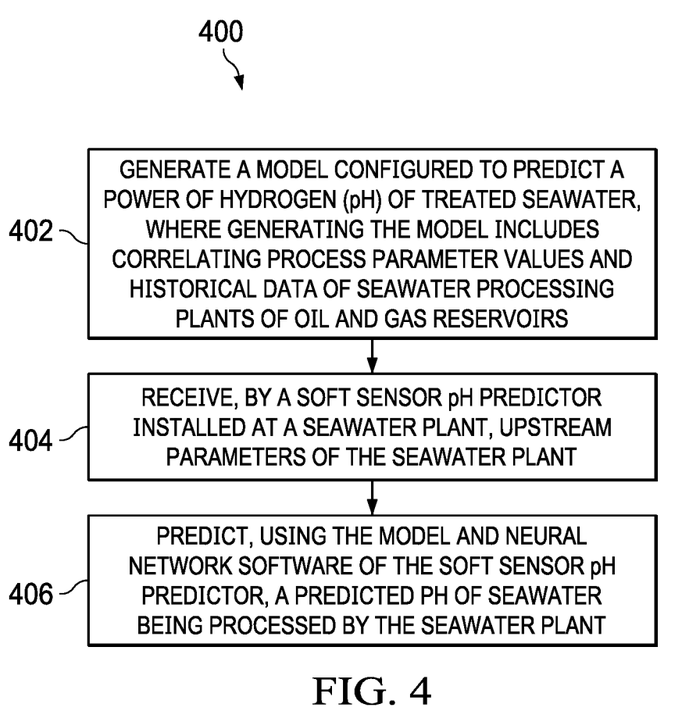
FIG. 4 is a flowchart of an example of a method for using a soft-sensor predict the pH in seawater, according to some implementations of the present disclosure.

FIG. 4 is a flowchart of an example of a method 400 for using a soft-sensor predict the pH in seawater, according to some implementations of the present disclosure. For clarity of presentation, the description that follows generally describes method 400 in the context of the other figures in this description. However, it will be understood that method 400 can be performed, for example, by any suitable system, environment, software, and hardware, or a combination of systems, environments, software, and hardware, as appropriate. In some implementations, various steps of method 400 can be run in parallel, in combination, in loops, or in any order.

At 402, a model is generated that is configured to predict a power of hydrogen (pH) of treated seawater. Generating the model includes correlating process parameter values and historical data of seawater processing plants of oil and gas water injection, as described with reference to FIGS. 1 and 2. In some implementations, generating the model can include performing and repeating a step test, including changing a single parameter during the step test by steps and analyzing data results. From 402, method 400 proceeds to 404.

At 404, upstream parameters of the seawater plant are received by a soft sensor pH predictor installed at a seawater plant. The upstream parameters can include, for example, a total seawater flow into a deaerator of the seawater plant, a seawater flow rate through each filter of the seawater plant, a temperature of seawater entering the deaerator, a flow of $N_2$ gas that is injected into the seawater, a flow of $SO_2$ solution that is injected into the seawater, and a level of seawater in the deaerator. From 404, method 400 proceeds to 406.

At 406, a pH of seawater being processed by the seawater plant is predicted using the model and neural network software of the soft sensor pH predictor. The treated seawater can be injected into an oil and gas reservoir, for example, to maintain a pressure of the oil and gas reservoir. In some implementations, predicted pH values can be validated using one or more of a lab sampling and a physical pH analyzer. After 406, method 400 can stop.

In some implementations, method 400 further includes removing dissolved oxygen (DO) from the seawater including injecting an $N_2$ gas and a $SO_2$ solution into the seawater. Removing the dissolved oxygen and lead to maintaining treated seawater at a pH value between 6.9 and 7.2, for example.

Figure 5:
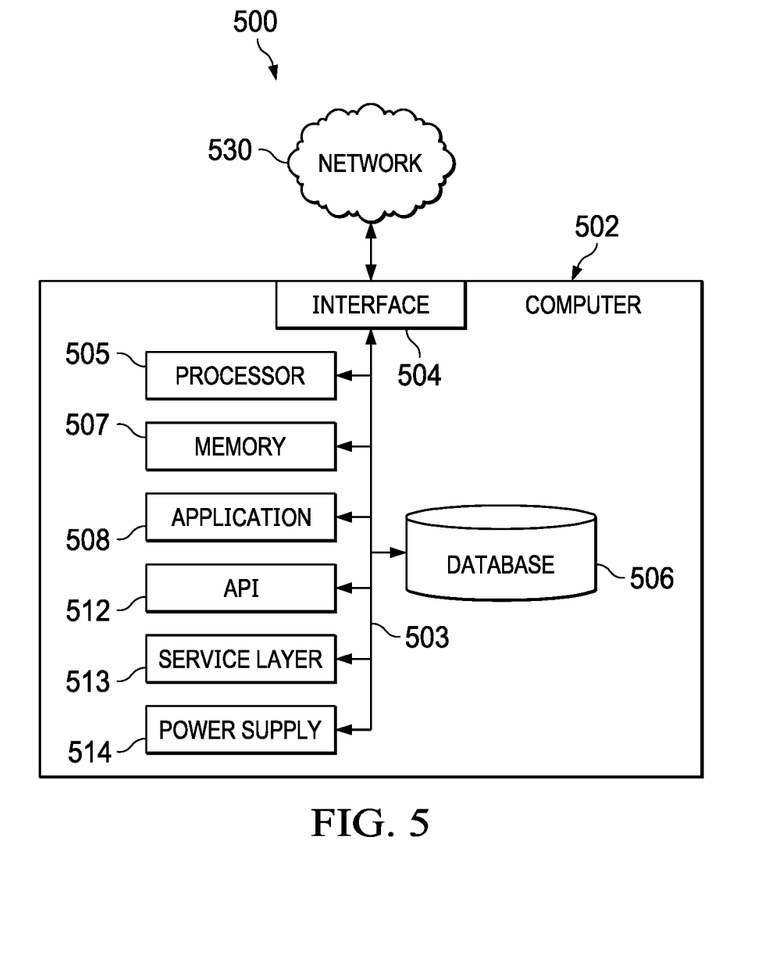
FIG. 5 is a block diagram illustrating an example computer system used to provide computational functionalities associated with described algorithms, methods, functions, processes, flows, and procedures as described in the present disclosure, according to some implementations of the present disclosure.

FIG. 5 is a block diagram of an example computer system 500 used to provide computational functionalities associated with described algorithms, methods, functions, processes, flows, and procedures described in the present disclosure, according to some implementations of the present disclosure. The illustrated computer 502 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 502 can include input devices such as keypads, keyboards, and touch screens that can accept user information. Also, the computer 502 can include output devices that can convey information associated with the operation of the computer 502. The information can include digital data, visual data, audio information, or a combination of information. The information can be presented in a graphical user interface (UI) (or GUI).

The computer 502 can serve in a role as a client, a network component, a server, a database, a persistency, or components of a computer system for performing the subject matter described in the present disclosure. The illustrated computer 502 is communicably coupled with a network 530. In some implementations, one or more components of the computer 502 can be configured to operate within different environments, including cloud-computing-based environments, local environments, global environments, and combinations of environments.

At a top level, the computer 502 is an electronic computing device operable to receive, transmit, process, store, and manage data and information associated with the described subject matter. According to some implementations, the computer 502 can also include, or be communicably coupled with, an application server, an email server, a web server, a caching server, a streaming data server, or a combination of servers.

The computer 502 can receive requests over network 530 from a client application (for example, executing on another computer 502). The computer 502 can respond to the received requests by processing the received requests using software applications. Requests can also be sent to the computer 502 from internal users (for example, from a command console), external (or third) parties, automated applications, entities, individuals, systems, and computers.

Each of the components of the computer 502 can communicate using a system bus 503. In some implementations, any or all of the components of the computer 502, including hardware or software components, can interface with each other or the interface 504 (or a combination of both) over the system bus 503. Interfaces can use an application programming interface (API) 512, a service layer 513, or a combination of the API 512 and service layer 513. The API 512 can include specifications for routines, data structures, and object classes. The API 512 can be either computer-language independent or dependent. The API 512 can refer to a complete interface, a single function, or a set of APIs.

The service layer 513 can provide software services to the computer 502 and other components (whether illustrated or not) that are communicably coupled to the computer 502. The functionality of the computer 502 can be accessible for all service consumers using this service layer. Software services, such as those provided by the service layer 513, can provide reusable, defined functionalities through a defined interface. For example, the interface can be software written in JAVA, C++, or a language providing data in extensible markup language (XML) format. While illustrated as an integrated component of the computer 502, in alternative implementations, the API 512 or the service layer 513 can be stand-alone components in relation to other components of the computer 502 and other components communicably coupled to the computer 502. Moreover, any or all parts of the API 512 or the service layer 513 can be implemented as child or sub-modules of another software module, enterprise application, or hardware module without departing from the scope of the present disclosure.

The computer 502 includes an interface 504. Although illustrated as a single interface 504 in FIG. 5, two or more interfaces 504 can be used according to particular needs, desires, or particular implementations of the computer 502 and the described functionality. The interface 504 can be used by the computer 502 for communicating with other systems that are connected to the network 530 (whether illustrated or not) in a distributed environment. Generally, the interface 504 can include, or be implemented using, logic encoded in software or hardware (or a combination of software and hardware) operable to communicate with the network 530. More specifically, the interface 504 can include software supporting one or more communication protocols associated with communications. As such, the network 530 or the interface's hardware can be operable to communicate physical signals within and outside of the illustrated computer 502.

The computer 502 includes a processor 505. Although illustrated as a single processor 505 in FIG. 5, two or more processors 505 can be used according to particular needs, desires, or particular implementations of the computer 502 and the described functionality. Generally, the processor 505 can execute instructions and can manipulate data to perform the operations of the computer 502, including operations using algorithms, methods, functions, processes, flows, and procedures as described in the present disclosure.

The computer 502 also includes a database 506 that can hold data for the computer 502 and other components connected to the network 530 (whether illustrated or not). For example, database 506 can be an in-memory, conventional, or a database storing data consistent with the present disclosure. In some implementations, database 506 can be a combination of two or more different database types (for example, hybrid in-memory and conventional databases) according to particular needs, desires, or particular implementations of the computer 502 and the described functionality. Although illustrated as a single database 506 in FIG. 5, two or more databases (of the same, different, or combination of types) can be used according to particular needs, desires, or particular implementations of the computer 502 and the described functionality. While database 506 is illustrated as an internal component of the computer 502, in alternative implementations, database 506 can be external to the computer 502.

The computer 502 also includes a memory 507 that can hold data for the computer 502 or a combination of components connected to the network 530 (whether illustrated or not). Memory 507 can store any data consistent with the present disclosure. In some implementations, memory 507 can be a combination of two or more different types of memory (for example, a combination of semiconductor and magnetic storage) according to particular needs, desires, or particular implementations of the computer 502 and the described functionality. Although illustrated as a single memory 507 in FIG. 5, two or more memories 507 (of the same, different, or combination of types) can be used according to particular needs, desires, or particular implementations of the computer 502 and the described functionality. While memory 507 is illustrated as an internal component of the computer 502, in alternative implementations, memory 507 can be external to the computer 502.

The application 508 can be an algorithmic software engine providing functionality according to particular needs, desires, or particular implementations of the computer 502 and the described functionality. For example, application 508 can serve as one or more components, modules, or applications. Further, although illustrated as a single application 508, the application 508 can be implemented as multiple applications 508 on the computer 502. In addition, although illustrated as internal to the computer 502, in alternative implementations, the application 508 can be external to the computer 502.

The computer 502 can also include a power supply 514. The power supply 514 can include a rechargeable or non-rechargeable battery that can be configured to be either user- or non-user-replaceable. In some implementations, the power supply 514 can include power-conversion and management circuits, including recharging, standby, and power management functionalities. In some implementations, the power-supply 514 can include a power plug to allow the computer 502 to be plugged into a wall socket or a power source to, for example, power the computer 502 or recharge a rechargeable battery.

There can be any number of computers 502 associated with, or external to, a computer system containing computer 502, with each computer 502 communicating over network 530. Further, the terms "client," "user," and other appropriate terminology can be used interchangeably, as appropriate, without departing from the scope of the present disclosure. Moreover, the present disclosure contemplates that many users can use one computer 502 and one user can use multiple computers 502.

Described implementations of the subject matter can include one or more features, alone or in combination.

For example, in a first implementation, a computer-implemented method includes the following. A model is generated that is configured to predict a power of hydrogen (pH) of treated seawater. Generating the model includes correlating process parameter values and historical data of seawater processing plants of oil and gas reservoirs. Upstream parameters of the seawater plant are received by a soft sensor pH predictor installed at a seawater plant. A pH of seawater being processed by the seawater plant is predicted using the model and neural network software of the soft sensor pH predictor.

The foregoing and other described implementations can each, optionally, include one or more of the following features:

A first feature, combinable with any of the following features, where the upstream parameters include a total seawater flow into a deaerator of the seawater plant, a seawater flow rate through each filter of the seawater plant, a temperature of seawater entering the deaerator, a flow of $N_2$ gas that is injected into the seawater, a flow of $SO_2$ solution that is injected into the seawater, and a level of seawater in the deaerator.

A second feature, combinable with any of the previous or following features, further including removing dissolved oxygen (DO) from the seawater including injecting an $N_2$ gas and a $SO_2$ solution into the seawater.

A third feature, combinable with any of the previous or following features, further including maintaining, based on the removing, treated seawater at a pH value between 6.9 and 7.2.

A fourth feature, combinable with any of the previous or following features, further including injecting the treated seawater into an oil and gas reservoir to maintain a pressure of the oil and gas reservoir.

A fifth feature, combinable with any of the previous or following features, where generating the model includes performing and repeating a step test, including changing a single parameter during the step test by steps and analyzing data results.

A sixth feature, combinable with any of the previous or following features, further including validating predicted pH values using one or more of a lab sampling and a physical pH analyzer.

In a second implementation, a non-transitory, computer-readable medium stores one or more instructions executable by a computer system to perform operations including the following. A model is generated that is configured to predict a power of hydrogen (pH) of treated seawater. Generating the model includes correlating process parameter values and historical data of seawater processing plants of oil and gas reservoirs. Upstream parameters of the seawater plant are received by a soft sensor pH predictor installed at a seawater plant. A pH of seawater being processed by the seawater plant is predicted using the model and neural network software of the soft sensor pH predictor.

The foregoing and other described implementations can each, optionally, include one or more of the following features:

A first feature, combinable with any of the following features, where the upstream parameters include a total seawater flow into a deaerator of the seawater plant, a seawater flow rate through each filter of the seawater plant, a temperature of seawater entering the deaerator, a flow of $N_2$ gas that is injected into the seawater, a flow of $SO_2$ solution that is injected into the seawater, and a level of seawater in the deaerator.

A second feature, combinable with any of the previous or following features, the operations further including removing dissolved oxygen (DO) from the seawater including injecting an $N_2$ gas and a $SO_2$ solution into the seawater.

A third feature, combinable with any of the previous or following features, the operations further including maintaining, based on the removing, treated seawater at a pH value between 6.9 and 7.2.

A fourth feature, combinable with any of the previous or following features, the operations further including injecting the treated seawater into an oil and gas reservoir to maintain a pressure of the oil and gas reservoir.

A fifth feature, combinable with any of the previous or following features, where generating the model includes performing and repeating a step test, including changing a single parameter during the step test by steps and analyzing data results.

A sixth feature, combinable with any of the previous or following features, the operations further including validating predicted pH values using one or more of a lab sampling and a physical pH analyzer.

In a third implementation, a computer-implemented system includes one or more processors and a non-transitory computer-readable storage medium coupled to the one or more processors and storing programming instructions for execution by the one or more processors. The programming instructions instruct the one or more processors to perform operations including the following. A model is generated that is configured to predict a power of hydrogen (pH) of treated seawater. Generating the model includes correlating process parameter values and historical data of seawater processing plants of oil and gas reservoirs. Upstream parameters of the seawater plant are received by a soft sensor pH predictor installed at a seawater plant. A pH of seawater being processed by the seawater plant is predicted using the model and neural network software of the soft sensor pH predictor.

The foregoing and other described implementations can each, optionally, include one or more of the following features:

A first feature, combinable with any of the following features, where the upstream parameters include a total seawater flow into a deaerator of the seawater plant, a seawater flow rate through each filter of the seawater plant, a temperature of seawater entering the deaerator, a flow of $N_2$ gas that is injected into the seawater, a flow of $SO_2$ solution that is injected into the seawater, and a level of seawater in the deaerator.

A second feature, combinable with any of the previous or following features, the operations further including removing dissolved oxygen (DO) from the seawater including injecting an $N_2$ gas and a $SO_2$ solution into the seawater.

A third feature, combinable with any of the previous or following features, the operations further including maintaining, based on the removing, treated seawater at a pH value between 6.9 and 7.2.

A fourth feature, combinable with any of the previous or following features, the operations further including injecting the treated seawater into an oil and gas reservoir to maintain a pressure of the oil and gas reservoir.

A fifth feature, combinable with any of the previous or following features, where generating the model includes performing and repeating a step test, including changing a single parameter during the step test by steps and analyzing data results.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/–R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method, comprising:
generating a model configured to predict a power of hydrogen (pH) of treated seawater output by a deaerator of a seawater processing plant, wherein generating the model comprises correlating process parameter values and historical data of the seawater processing plant of oil and gas reservoirs, the seawater processing plant comprising a temporary PH analyzer used for developing the model;
receiving, by a soft sensor pHI predictor installed at the seawater processing plant, upstream parameters of the seawater processing plant, the seawater processing plant having the temporary PH analyzer removed after developing the model;
predicting, using the model and a neural network software of the soft sensor pH predictor, the pH of treated seawater processed by the seawater processing plant;
removing dissolved oxygen (DO) from seawater to adjust the pH of treated seawater processed by the seawater processing plant to be within a target range pH of seawater; and
injecting, by a flow controller, the treated seawater into an oil and gas reservoir to maintain a pressure of the oil and gas reservoir.

2. The computer-implemented method of claim 1, wherein the upstream parameters comprise a total seawater flow into a deaerator of the seawater processing plant, a seawater flow rate through each filter of the seawater processing plant, a temperature of seawater entering the deaerator, a flow of $N_2$ gas that is injected into the seawater, a flow of $SO_2$ solution that is injected into the seawater, and a level of seawater in the deaerator.

3. The computer-implemented method of claim 1, wherein removing the DO from the seawater comprises injecting an $N_2$ gas and a $SO_2$ solution into the seawater.

4. The computer-implemented method of claim 3, further comprising maintaining, based on the removing, treated seawater at a pH value between 6.9 and 7.2.

5. The computer-implemented method of claim 1, wherein the flow controller comprises a plurality of flow controllers coupled to a mathematical block.

6. The computer-implemented method of claim 1, wherein generating the model comprises performing and repeating a step test, comprising changing a single parameter during the step test by steps and analyzing data results.

7. The computer-implemented method of claim 1, further comprising validating predicted pH values using one or more of a lab sampling and a physical pH analyzer.

8. A non-transitory, computer-readable medium storing one or more instructions executable by a computer system to perform operations comprising:
generating a model configured to predict a power of hydrogen (pH) of treated seawater output by a deaerator of a seawater processing plant, wherein generating the model comprises correlating process parameter values and historical data of the seawater processing plant of oil and gas reservoirs, the seawater processing plant comprising a temporary PH analyzer used for developing the model;
receiving, by a soft sensor pH predictor installed at the seawater processing plant, upstream parameters of the seawater processing plant, the seawater processing plant having the temporary PH analyzer removed after developing the model;
predicting, using the model and a neural network software of the soft sensor pH predictor, the pH of treated seawater processed by the seawater processing plant;
removing dissolved oxygen (DO) from seawater to adjust the pH of treated seawater processed by the seawater processing plant to be within a target range pH of seawater; and
injecting, by a flow controller, the treated seawater into an oil and gas reservoir to maintain a pressure of the oil and gas reservoir.

9. The non-transitory, computer-readable medium of claim 8, wherein the upstream parameters comprise a total seawater flow into a deaerator of the seawater processing plant, a seawater flow rate through each filter of the seawater processing plant, a temperature of seawater entering the deaerator, a flow of $N_2$ gas that is injected into the seawater, a flow of $SO_2$ solution that is injected into the seawater, and a level of seawater in the deaerator.

10. The non-transitory, computer-readable medium of claim 8, the operations further comprising removing dissolved oxygen (DO) from the seawater comprising injecting an $N_2$ gas and a $SO_2$ solution into the seawater.

11. The non-transitory, computer-readable medium of claim 10, the operations further comprising maintaining, based on the removing, treated seawater at a pH value between 6.9 and 7.2.

12. The non-transitory, computer-readable medium of claim 8, wherein the flow controller comprises a plurality of flow controllers coupled to a mathematical block.

13. The non-transitory, computer-readable medium of claim 8, wherein generating the model comprises performing and repeating a step test, comprising changing a single parameter during the step test by steps and analyzing data results.

14. The non-transitory, computer-readable medium of claim 8, the operations further comprising validating predicted pH values using one or more of a lab sampling and a physical pH analyzer.

15. A computer-implemented system, comprising:
one or more processors; and
a non-transitory computer-readable storage medium coupled to the one or more processors and storing programming instructions for execution by the one or more processors, the programming instructions instructing the one or more processors to perform operations comprising:
generating a model configured to predict a power of hydrogen (pH) of treated seawater output by a deaerator of a seawater processing plant, wherein generating the model comprises correlating process parameter values and historical data of the seawater processing plant of oil and gas reservoirs, the seawater processing plant comprising a temporary PH analyzer used for developing the model;
receiving, by a soft sensor pH predictor installed at the seawater processing plant, upstream parameters of the seawater processing plant, the seawater processing plant having the temporary PH analyzer removed after developing the model;
predicting, using the model and a neural network software of the soft sensor pH predictor, the pH of treated seawater processed by the seawater processing plant;
removing dissolved oxygen (DO) from seawater to adjust the pH of treated seawater processed by the seawater processing plant to be within a target range pH of seawater; and injecting, by a flow controller, the treated seawater into an oil and gas reservoir to maintain a pressure of the oil and gas reservoir.

16. The computer-implemented system of claim 15, wherein the upstream parameters comprise a total seawater flow into a deaerator of the seawater processing plant, a seawater flow rate through each filter of the seawater processing plant, a temperature of seawater entering the deaerator, a flow of $N_2$ gas that is injected into the seawater, a flow of $SO_2$ solution that is injected into the seawater, and a level of seawater in the deaerator.

17. The computer-implemented system of claim 15, the operations further comprising removing dissolved oxygen (DO) from the seawater comprising injecting an $N_2$ gas and a $SO_2$ solution into the seawater.

18. The computer-implemented system of claim 17, the operations further comprising maintaining, based on the removing, treated seawater at a pH value between 6.9 and 7.2.

19. The computer-implemented system of claim 15, wherein the flow controller comprises a plurality of flow controllers coupled to a mathematical block.

20. The computer-implemented system of claim 15, wherein generating the model comprises performing and repeating a step test, comprising changing a single parameter during the step test by steps and analyzing data results.

* * * * *

UNITED STATES PATENT AND TRADEMARK OFFICE
CERTIFICATE OF CORRECTION

| | |
|---|---|
| PATENT NO. | : 12,260,312 B2 |
| APPLICATION NO. | : 17/140224 |
| DATED | : March 25, 2025 |
| INVENTOR(S) | : Prafulchandra Bhavanbhai Sonara and Abdulrahman S. Al Johar |

It is certified that error appears in the above-identified patent and that said Letters Patent is hereby corrected as shown below:

On the Title Page

Item [56], Column 2, Line 1, please replace "CN" with -- JP --

In the Claims

In Column 15, Line 11, Claim 1, please replace "pHI" with -- pH --

Signed and Sealed this
Thirteenth Day of May, 2025

Coke Morgan Stewart
*Acting Director of the United States Patent and Trademark Office*